(12) United States Patent
Beaussoubre et al.

(10) Patent No.: US 11,141,366 B2
(45) Date of Patent: Oct. 12, 2021

(54) PERFUMING COMPOSITION

(71) Applicant: FIRMENICH SA, Satigny (CH)

(72) Inventors: Pascal Beaussoubre, Geneva (CH); Wolfgang Fieber, Geneva (CH); Aude Daugeron-Jouault, Geneva (CH)

(73) Assignee: Firmenich SA, Satigny (CH)

(*) Notice: Subject to any disclaimer, the term of this patent is extended or adjusted under 35 U.S.C. 154(b) by 72 days.

(21) Appl. No.: 16/611,537

(22) PCT Filed: May 8, 2018

(86) PCT No.: PCT/EP2018/061836
§ 371 (c)(1),
(2) Date: Nov. 7, 2019

(87) PCT Pub. No.: WO2018/206559
PCT Pub. Date: Nov. 15, 2018

(65) Prior Publication Data
US 2021/0145715 A1    May 20, 2021

(30) Foreign Application Priority Data
May 11, 2017    (EP) .................................... 17170618

(51) Int. Cl.
*A61K 8/34* (2006.01)
*A61Q 13/00* (2006.01)

(52) U.S. Cl.
CPC .............. *A61K 8/345* (2013.01); *A61Q 13/00* (2013.01)

(58) Field of Classification Search
CPC .................................. A61K 8/345; A61Q 13/00
See application file for complete search history.

(56) References Cited

U.S. PATENT DOCUMENTS 4,225,515 A * 9/1980 Weber .................... C11B 9/0042
568/444
5,585,343 A * 12/1996 McGee .................. A61K 8/068
512/1

FOREIGN PATENT DOCUMENTS

DE    2307627 A1    9/1974
WO    9512379 A1    5/1995

OTHER PUBLICATIONS

International Search Report and Written Opinion for International Application No. PCT/EP2018/061836, dated Jul. 2, 2018. 14 pages.
Werle et al., "Alcohols, Polyhydric", Ullmann's Encclopedia of Industrial Chemistry, Published Jul. 15, 2008, pp. 263-284, vol. 2.

* cited by examiner

*Primary Examiner* — Arrie L Reuther
(74) *Attorney, Agent, or Firm* — Armstrong Teasdale LLP

(57) ABSTRACT

Described herein is a stable perfuming composition including a perfume oil, a viscosifying agent including tricyclodecanedimethanol alcohol, and a perfumery carrier including hexylene glycol.
Also described herein is the use of hexylene glycol in a composition including tricyclodecanedimethanol alcohol and a perfume oil to prevent the crystallization of the composition.

20 Claims, No Drawings

PERFUMING COMPOSITION

CROSS-REFERENCE TO RELATED APPLICATIONS

This application is a U.S. National Phase Application of PCT/EP2018/061836, filed on May 8, 2018, which claims the benefit of priority to European Patent Application Number 17170618.7, filed May 11, 2017, the entire contents of which are hereby incorporated by reference herein.

TECHNICAL FIELD

The present invention relates to the field of perfuming compositions. More particularly, the present invention describes a stable perfuming composition comprising a perfume oil, a viscosifying agent comprising tricyclodecanedimethanol alcohol, and a perfumery carrier comprising hexylene glycol.

The use of hexylene glycol in a perfuming composition comprising tricyclodecanedimethanol alcohol to prevent the crystallization of said composition is also an object of the invention.

BACKGROUND OF THE INVENTION

Tricyclodecanedimethanol alcohol (also known as TCD alcohol DM) is a highly viscous additive used for viscous perfumed composition.

It is known that TCD alcohol DM tends to crystallize or even gel upon storage at room temperature.

Thus, when incorporated in consumer products comprising a perfume oil, tricyclodecanedimethanol alcohol needs to be heated up to become transparent and more fluid.

However, upon storage, a recrystallization occurs in final consumer products leading to a difficult anticipation of the shelf life of the final product upon storage condition.

Some highly viscous oils (called "Mukhallat") are available on the market. Those compositions comprise TCD alcohol DM, perfume and dipropylene glycol. However, it has been observed that they crystallize upon time, rendering the perfuming composition less appealing, and even unusable in some cases.

There is therefore a need to provide viscous perfumed composition that would be stable upon storage.

To our knowledge, no prior art deals with the prevention of crystallization of TCD alcohol DM in perfuming composition.

The composition of the invention solves this problem as it contains a specific additive in addition to TCD alcohol DM that prevents the crystallization of the composition upon time.

SUMMARY OF THE INVENTION

A first object of the invention is a perfuming composition comprising:
  a viscosifying agent comprising tricyclodecanedimethanol alcohol,
  a perfume oil comprising at least one perfuming ingredient;
  at least one perfumery carrier comprising hexylene glycol,
  optionally, a perfuming adjuvant,
  wherein the weight ratio between tricyclodecanedimethanol alcohol and hexylene glycol in the perfuming composition is from 0.1 to 15.

A second object of the invention is a process for manufacturing the composition as defined above.

A third object is a consumer product comprising the composition as defined above.

Finally, a last object of the invention is the use of hexylene glycol in a perfuming composition comprising tricyclodecanedimethanol alcohol and a perfume oil comprising at least one perfuming ingredient to prevent crystallization of said composition upon time.

DETAILED DESCRIPTION OF THE INVENTION

Unless stated otherwise, percentages (%) are meant to designate percent by weight of a composition.

Perfuming Composition

The present invention has now determine a way to prevent the crystallisation of a composition comprising tricyclodecanedimethanol alcohol and a perfume oil by using hexylene glycol as an additive into the composition.

A first object of the invention is therefore a perfuming composition comprising:
  a viscosifying agent comprising tricyclodecanedimethanol alcohol,
  a perfume oil comprising at least one perfuming ingredient;
  at least one perfumery carrier comprising hexylene glycol,
  optionally, a perfuming adjuvant,
  wherein the weight ratio between tricyclodecanedimethanol alcohol and hexylene glycol in the perfuming composition is from 0.1 to 15.

The composition of the invention is a one-phase composition. In other words, a two-phase composition such as an emulsion is not included in this definition.

The composition of the present invention is transparent at room temperature (RT).

By "room temperature", it should be understood a temperature comprised between 20 and 25° C.

The term transparent means that the solution in the absence of coloring or fluorescent agents, has transmittance values in the visible light (500-800 nm) of 100% at a path length of 1 cm referenced against demineralized water.

However, it should be understood that the composition according to the invention can comprise coloring agent(s) while being transparent.

Typically, the composition of the invention has a turbidity less than 10 NTU, preferably less than 5 NTU, more preferably between 0.01 and 5 NTU.

The composition has preferably a viscosity greater than 500 mPa·s at 20° C., more preferably between 500 and 5000 mPa·s, more preferably between 2000 and 5000 mPa·s at 20° C.

Viscosity can be measured by using the rheometer AR-2000 model of TA Instruments V5.4.0 at a shear rate of 21 s$^{-1}$.

Perfume Oil

According to the invention, perfume oil comprises at least one perfuming ingredient.

By "perfume oil" (or also "perfume" or "fragrance") what is meant here is an ingredient or composition that is a liquid at about 20° C. According to any one of the above embodiments said perfume oil can be a perfuming ingredient alone or a mixture of ingredients in the form of a perfuming composition. As a "perfuming ingredient" it is meant here a compound, which is used for the primary purpose of conferring or modulating an odour. In other words such an ingredient, to be considered as being a perfuming one, must be recognized by a person skilled in the art as being able to at least impart or modify in a positive or pleasant way the odor of a composition, and not just as having an odor. For the purpose of the present invention, perfume oil also includes combination of perfuming ingredients with substances which together improve, enhance or modify the delivery of the perfuming ingredients, such as perfume precursors, as well as combinations which impart an additional benefit beyond that of modifying or imparting an odor, such as long-lasting, blooming, malodour counteraction, antimicrobial effect, microbial stability, insect control.

The nature and type of the perfuming ingredients present in the perfume oil do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said ingredients may also be compounds known to release in a controlled manner various types of perfuming compounds.

The perfuming ingredients may be dissolved in a solvent of current use in the perfume industry. Examples of such solvents are glycol/diol (such as dipropyleneglycol), diethyl phthalate, triethyl citrate, benzyl benzoate, isopropyl myristate, abalyn.

According to a particular embodiment, the perfuming composition is ethanol free.

It is also understood that perfuming ingredients can be admixed with compounds known to release in a controlled manner various types of perfuming ingredients, namely through chemical reaction cleavage of chemical bonds of higher molecular weight precursors. Such chemical release molecules are generally designated as "profragrances" or "perfume release systems" and they are commonly used in fragrances to prolong the release in time of specific odorants and their olfactive impact over time, as compared to the olfactive effect that each such odorant could produce when used as such and not in the form of an heavier precursor thereof.

According to an embodiment, the perfume oil comprises at least one perfume raw material chosen in the group consisting of aldehydes, alcools, esters, ketones, ethers and mixtures thereof. According to a particular embodiment, the perfume oil comprises at least one perfume raw material chosen in the ingredients in table 1.

TABLE 1

| Perfume raw materials | |
| --- | --- |
| Chemical name | Common name |
| 3-HYDROXY-2-METHYL-4H-PYRAN-4-ONE | MALTOL |
| 2-ETHYL-3-HYDROXY-4(4H)-PYRANONE | ETHYL MALTOL |
| 4-(4-HYDROXYPHENYL)-2-BUTANONE | RASPBERRY KETONE |
| 4-HYDROXY-3-METHOXYBENZALDEHYDE | VANILLIN |
| 3-(1,3-BENZODIOXOL-5-YL)-2-METHYLPROPANAL | HELIONAL |
| 2-METHOXYPHENOL | GUAIACOL |
| BENZALDEHYDE | |
| 2-CHROMENONE | COUMARINE |
| 2-PHENYLETHANOL | |
| 4-METHOXYBENZALDEHYDE | |
| 7-METHYL-2H-1,5-BENZODIOXEPIN-3(4H)-ONE | CALONE ® * |
| INDOLE | INDOL |
| PHENYLACETALDEHYDE | |
| 2-METHOXY-4-(2-PROPEN-1-YL)PHENOL | EUGENOL |
| (2E)-2-METHYL-3-(4-METHYLPHENYL)-2-PROPEN-1-OL | JOSENOL ® * |
| ETHYL 2,3-EPOXY-3-PHENYLBUTANOATE | |
| 2,4-DIMETHYL-3-CYCLOHEXENE-1-CARBALDEHYDE | ZESTOVER |
| BENZYL PROPANOATE | |
| 2,4-DIMETHYL-4,4A,5,9B-TETRAHYDROINDENO[1,2-D][1,3]DIOXINE | MAGNOLAN |
| 4-NONANOLIDE | GAMMA NONALACTONE |
| 2,6,6-TRIMETHYL-1,3-CYCLOHEXADIENE-1-CARBALDEHYDE | SAFRANAL |
| 4-ETHYLPHENOL | |
| 7-ISOPROPYL-2H,4H-1,5-BENZODIOXEPIN-3-ONE | CASCALONE ® * |
| ALLYL (CYCLOHEXYLOXY)ACETATE | CYCLOGALBANATE |
| 3-(4-TERT-BUTYLPHENYL)PROPANAL | BOURGEONAL |
| METHYL (2E)-2-METHYL-2-HEXENOATE | |
| METHYL 2-((1RS,2R5)-3-OXO-2-PENTYLCYCLOPENTYL)ACETATE | HEDIONE ® * |
| 3,7-DIMETHYL-1,6-OCTADIEN-3-OL | LINALOL |
| (R)-3,7-DIMETHYL-6-OCTENENITRILE | |
| 1,3-NONANEDIYL DIACETATE + TETRAHYDRO-3-PENTYL-4(2H)-PYRANYL ACETATE | JASMAL |
| 2,6-DIMETHYL-5-HEPTENAL | MELONAL |
| CYCLHEXYLIDENE(PHENYL)ACETONITRILE | PEONILE ® ** |
| 5-HEPTYLDIHYDRO-2(3H)-FURANONE | GAMMA UNDECALACTONE |

TABLE 1-continued

| Perfume raw materials | |
|---|---|
| Chemical name | Common name |
| (2E)-1-(2,6,6-TRIMETHYL-1,3-CYCLOHEXADIEN-1-YL)-2-BUTEN-1-ONE | DAMASCENONE |
| 3,7-DIMETHYL-6-OCTEN-1-OL | CITRONELLOL |
| 2,3,3-TRIMETHYL-1-INDANONE | SAFRALEINE ™ ** |
| 4-METHYL-2-(2-METHYL1-PROPEN-1-YL)TETRAHYDRO-2H-PYRAN | ROSE OXIDE |
| METHYL2-NONYNOATE | |
| 3-(3-ISOPROPYL-1-PHENYL)BUTANAL | FLORHYDRAL ™ ** |
| 3,7-DIMETHYL-1,6-NONADIEN-3-OL | ETHYL LINALOL |
| 3-(4-ISOPROPYLPHENYL)-2-METHYLPROPANAL | |
| ALLYL HEXANOATE | |
| (2E)-1-(2,6,6-TRIMETHYL-1-CYCLOHEXEN-1-YL)-2-BUTEN-1-ONE | DORINONE BETA |
| (2E)-1-(2,6,6-TRIMETHYL-2-CYCLOHEXEN-1-YL)-2-BUTEN-1-ONE | DAMASCONE ALPHA |
| 1,2,3,5,6,7-HEXAHYDRO-1,1,2,3,3-PENTAMETHYL-4-INDENONE | CASHMERAN ® *** |
| (A) + (+−)-3,5,6,6-TETRAMETHYL-4-METHYLIDENE-2-HEPTANONE (B) + | KOAVONE ® *** |
| (+−)-(4E)-3,4,5,6,6-PENTAMETHYL-4-HEPTEN-2-ONE(C) +(+−)-(3Z)-3,4,5,6,6- | |
| PENTAMETHYL-3-HEPTEN-2-ONE (D) + (+−)-(3E)-3,4,5,6,6-PENTAMETHYL-3- | |
| HEPTEN-2-ONE (E) | |
| 1-ETHOXY-4-(1-ETHOXYVINYL)-3,3,5,5-TETRAMETHYLCYCLOHEXENE | KEPHALIS |
| (A) + 4-(1-ETHOXYVINYL)-3,3,5,5-TETRAMETHYLCYCLOHEXANONE (B) | |
| 2-ETHOXYNAPHTHALENE | |
| PERHYDRO-4ALPHA,8ABETA-DIMETHYL-4A-NAPHTHALENOL | |
| 4-CYCLOHEXYL-2-METHYL-2-BUTANOL | CORANOL |
| 10-UNDECENAL | |
| (E)-TRANS-ALPHA-IRONE + (E)-CIS-ALPHA-IRONE + (E)-BETA-IRONE | IRONE ALPHA |
| 8-SEC-BUTYLQUINOLINE + 6-SEC-BUTYLQUINOLINE | ISOBUTYLQUINOLEINE |
| 3-(4-METHYL-3-PENTEN-1-YL)-3-CYCLOHEXENE-1-CARBALDEHYDE + 4-(4- | |
| METHYL-3-PENTEN-1-YL)-3-CYCLOHEXENE-1-CARBALDEHYDE | |
| TRICYCLO[5.2.1.0(2,6)]DEC-3-EN-8-YL PROPANOATE + | |
| TRICYCLO[5.2.1.0(2,6)]DEC-4-EN-8-YL PROPANOATE | |
| 2-(2-METHYL-2-PROPANYL)CYCLOHEXYL ACETATE | VERDOX ™*** |
| 1,4-DIOXACYCLOHEPTADECANE-5,17-DIONE | ASTROTONE |
| ALLYL 3-CYCLOHEXYLPROPANOATE | |
| 3-METHYL-5-(2,2,3-TRIMETHYL-3-CYCLOPENTEN-1-YL)-2-PENTANOL | SANDALORP ® ** |
| {1-METHYL-2-{(1,2,2-TRIMETHYLBICYCLO[3.1.0]HEX-3- | JAVANOL ® ** |
| YL)METHYL]CYCLOPROPYL}METHANOL | |
| (3E)-3-METHYL-4-(2,6,6-TRIMETHYL-2-CYCLOHEXEN-1-YL)-3-BUTEN-2-ONE + | ISORALDEINE |
| (1E)-1-(2,6,6-TRIMETHYL-2-CYCLOHEXEN-1-YL)-1-PENTEN-3-ONE | |
| (4Z,8E)-1,5,8-TRIMETHYL-13-OXABICYCLO[10.1.0]TRIDECA-4,8-DIENE + (4Z,8E)- | CEDROXYDE |
| 1,4,8-TRIMETHYL-13-OXABICYCLO[10.1.0]TRIDECA-4,8-DIENE | |
| 1-METHYL-4-(4-METHYL-3-PENTENYL)-3-CYCLOHEXENE-1-CARBALDEHYDE | PRECYCLEMONE B |
| 1-(2,3,8,8-TETRAMETHYL-1,2,3,4,5,6,7,8-OCTAHYDRO-2- | ISO E SUPER ® *** |
| NAPHTHALENYL)ETHANONE + 1-(2,3,8,8-TETRAMETHYL-1,2,3,4,6,7,8,8A- | |
| OCTAHYDRO-2-NAPHTHALENYL)ETHANONE + 1-(2,3,8,8-TETRAMETHYL- | |
| 1,2,3,5,6,7,8,8A-OCTAHYDRO-2-NAPHTHALENYL)ETHANONE | |
| METHYL N-(7-HYDROXY-3,7-DIMETHYL-1-OCTENYL)ANTHRANILATE | ANTHRANILOL |
| 1-(3,5,5,6,8,8-HEXAMETHYL-5,6,7,8-TETRAHYDRO-2-NAPHTHALENYL) | TONALIDE |
| ETHANONE | |
| 1-[(1RS,6SR)-2,2,6-TRIMETHYLCYCLOHEXYL]-3-HEXANOL | NORLIMBANOL ® * |
| 1-(6-TERT-BUTYL-1,1-DIMETHYL-4-INDANYL)-1-ETHANONE | MUSK DTI |
| 1-(2,3,8,8-TETRAMETHYL-1,2,3,4,5,6,7,8-OCTAHYDRO-2- | DERAMBRENE |
| NAPHTHALENYL)ETHANONE + 1-(2,3,8,8-TETRAMETHYL-1,2,3,4,6,7,8,8A- | |
| OCTAHYDRO-2-NAPHTHALENYL)ETHANONE + 1-(2,3,8,8-TETRAMETHYL- | |
| 1,2,3,5,6,7,8,8A-OCTAHYDRO-2-NAPHTHALENYL)ETHANONE | |
| CEDRAN-8-YL ACETATE | |
| (3ARS,5ASR,9ASR,9BRS)-3A,6,6,9A- | CETALOX ® * |
| TETRAMETHYLDODECAHYDRONAPHTHO[2,1-B]FURAN | |
| 1-(2,2,3,6-TETRAMETHYL-CYCLOHEXYL)-3-HEXANOL | LIMBANOL ® * |
| (4E)-3-METHYL-4-CYCLOPENTADECEN-1-ONE + (5E)-3-METHYL-5- | MUSCENONE ® DELTA |
| CYCLOPENTADECEN-1-ONE + -(5Z)-3-METHYL-5-CYCLOPENTADECEN-1-ONE | |
| (3AR,5A5,9A5,9BR)-3A,6,6,9A-TETRAMETHYLDODECAHYDRONAPHTH0(2,1- | AMBROX ® * |
| B]FURAN | |
| (3ARS,5ASR,9ASR,9BSR)-3A,6,6,9A- | CACHALOX ® * |
| TETRAMETHYLDODECAHYDRONAPHTHO[2,1-B]FURAN | |
| 8-METHOXYCEDRANE | CEDRAMBER |
| 2/3/4-(5,5,6-TRIMETHYLBICYCLO[2.2.1]HEPT-2-YL)-1-CYCLOHEXANOL + 2- | SANDELA ® ** |
| (1,7,7-TRIMETHYLBICYCLO[2.2.1]HEPT-2-YL)-1-CYCLOHEXANOL | |
| CEDRAN-8-YL ACETATE | |

* Origin: Firmenich SA, Geneva, Switzerland
** Origin: Givaudan SA, Vernier, Suisse
*** Origin: International Flavors & Fragrances, USA According to an embodiment, the composition comprises up to 50% by weight of perfume oil based on the total weight of the composition.

The composition comprises preferably from 3% to 50%, more preferably from 10% to 30%, even more preferably from 15% to 20% by weight of perfume oil based on the total weight of the composition.

According to a particular embodiment, perfume oil is mixed with another ingredient selected from the group consisting of nutraceuticals, cosmetics, insect control agents and biocide actives.

According to a particular embodiment, the oil phase consists of a perfume oil.

Viscosifying Agent

According to the invention, the perfuming composition comprises a viscosifying agent comprising tricyclodecanedimethanol alcohol.

According to an embodiment, the viscosifying agent consists of tricyclodecanedimethanol alcohol.

According to an embodiment, the composition comprises at least 5%, preferably at least 10%, more preferably at least 50% by weight of tricyclodecanedimethanol alcohol based on the total weight of the composition.

The composition comprises preferably from 5% to 70%, preferably from 20% to 70%, even more preferably from 50% to 60% by weight of tricyclodecanedimethanol alcohol based on the total weight of the composition.

Tricyclodecanedimethanol alcohol (TCD alcohol DM) is commercially available from OXEA, GmbH.

Perfumery Carrier

The perfuming composition of the invention comprises a perfumery carrier to solubilize the perfume oil and to adjust the viscosity of the perfuming composition.

It has been found that hexylene glycol could retard and/or prevent significantly the recrystallization of TCD alcohol DM when incorporated in a perfuming composition.

Thus, the present invention is characterized by the fact that the perfumery carrier comprises hexylene glycol (2-methylpentane-2,4-diol).

According to an embodiment, the composition comprises up to 40% by weight of hexylene glycol based on the total weight of the perfuming composition.

The composition comprises preferably from 4% to 40%, more preferably from 10% to 25% by weight of hexylene glycol based on the total weight of the composition.

According to the invention, the weight ratio between tricyclodecanedimethanol alcohol and hexylene glycol is from 0.1 to 15, preferably from 0.5 to 10, more preferably from 0.5 to 5.

According to another embodiment, the perfumery carrier further comprises co-solvents preferably chosen in the group consisting of dipropylene glycol, glycerol, 1,2-pentanediol, 1,2-hexanediol, D,L-1,2-isopropylidene glycerol propanediol, butanediol and mixtures thereof.

According to a particular embodiment, the co-solvent is dipropylene glycol.

According to an embodiment, co-solvent(s) is (are) used in an amount between 0 and 30%, preferably between 5 and 30% by weight based on the total weight of the perfuming composition.

Optional Aqueous Phase

According to a particular embodiment, the composition comprises an aqueous phase preferably in an amount comprised between 0.01 and 1% by weight based on the total weight of the composition.

Optional Perfumery Adjuvant(s)

The composition of the invention can further comprise perfumery adjuvant.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

As non-limiting examples, one may cite coloring agents, preservatives, pH adjuster, antioxydants, chelating agents, UV filters, quenchers, silicon oils, and mixture thereof.

Such optional perfumery adjuvant will represent no more than 5% w/w, or even 2% w/w, the percentages being relative to the total weight of the composition.

According to a particular embodiment, the perfuming composition comprises, preferably consists of:
  from 3% to 50%, more preferably from 10% to 30%, even more preferably from 15% to 20% of a perfume oil;
  from 5% to 70%, preferably from 20% to 70%, even more preferably from 50% to 60% by weight of tricyclodecanedimethanol alcohol, and
  from 4% to 40%, more preferably from 10% to 25% by weight of hexylene glycol,
  from 0 to 30%, preferably from 5 and 30% by weight of a co-solvent, and
  from 0 to 5%, preferably from 0 to 2% by weight of a perfumery adjuvant.

Process for Preparing a Perfuming Composition

Another object of the invention is a process for manufacturing a perfuming composition comprising the steps consisting of:
  (i) Heating tricyclodecanedimethanol alcohol at a temperature comprised preferably between 70° C. and 120° C.,
  (ii) Cooling down the mixture obtained in step i) before adding the perfume oil,
  wherein hexylene glycol is added in step (i) or in step (ii)
  wherein the weight ratio between tricyclodecanedimethanol alcohol and hexylene glycol in the perfuming composition is from 0.1 to 15.

According to a particular embodiment, tricyclodecanedimethanol alcohol is heated between 90° C. and 120° C., preferably between 100° C. and 120° C. since it has been found that the prevention of crystallization is particularly significant when tricyclodecanedimethanol alcohol is heated at high temperatures.

According to an embodiment, in step ii) mixture is cooled down at a temperature comprised between 20 and 40° C.

If water and/or co-solvents are present in the composition, they are added either in step (i) or in step (ii) according to the heating temperature and their boiling point.

All the technical features previously described for the perfuming composition also apply for the process defined above.

Another object of the invention is a perfuming composition obtainable by the process defined above.

Another object of the invention is a consumer product, preferably in the form of a fine fragrance product or an air freshener product comprising the composition as defined above.

Fine fragrance products are preferably in the form of a perfume concentrates, perfumes, extract, mukhallat, attar.

Another object of the invention is the use of hexylene glycol in a perfuming composition comprising tricyclodecanedimethanol alcohol and a perfume oil to prevent crystallization of tricyclodecanedimethanol alcohol.

Another object of the invention is a method for preventing crystallization in a perfuming composition comprising tri-cyclodecanedimethanol alcohol and a perfume oil by adding hexylene glycol to said composition.

The invention will now be further described by way of examples. It will be appreciated that the invention as claimed is not intended to be limited in any way by these examples.

EXAMPLES

Sample preparation: In all examples below, tricyclodecanedimethanol alcohol (TCD alcohol DM), hexylene glycol, and optionally co-solvents and/or water are mixed together using a spatula. Using a water bath, the mix is then heated up to 70° C. (or to 90° C.) in a closed vial under magnetic stirring. The sample is let to stir at 70° C. (or 90° C.) for 1hr to allow the complete "visual" solubilization of TCD alcohol DM. Then the mix is cooled down to room temperature, and the fragrance is added and mixed with a spatula.

Stability performance: In all examples below, stability to crystallization was visually assessed as a function of time. The beginning of crystallization generally results in a cloudy aspect of the sample and evolves towards a strong precipitation and deposition of small crystals at the bottom of the sample.

Perfume oil: The following perfume oils were used in the examples (see table 1-a to table d)

TABLE 1-a

Composition of fragrance F1

| Ingredient | % wt |
|---|---|
| Hedione ® [1] | 1 |
| Habanolide ® [2] | 20 |
| Exaltolide ® [3] | 60 |
| Ambrox ® [4] | 1 |
| Helvetolide ® [5] | 6 |
| Muscenone ® delta [6] | 12 |
| Total mass % | 100 |

[1] Methyl dihydrojasmonate, Firmenich SA, Geneva, Switzerland
[2] Pentadecenolide, Firmenich SA, Geneva, Switzerland
[3] Pentadecanolide, Firmenich SA, Geneva, Switzerland
[4] (—)-(8R)-8,12-epoxy-13,14,15,16-tetranorlabdane, Firmenich SA, Geneva, Switzerland
[5] (1S,1'R)-2-[1-(3',3'-dimethyl-1'-cyclohexyl)ethoxy]-2-methylpropyl propanoate, Firmenich SA, Geneva, Switzerland
[6] 3-Methyl-5-cyclopentadecen-1-one, Firmenich SA, Geneva, Switzerland TABLE 1-b Composition of fragrance F2

| Ingredients | Parts |
|---|---|
| TRIETHYLCITRATE | 6880 |
| DIPROPYLENGLYCOL | 2400 |
| ISO E SUPER [1] | 600 |
| AMBROX ® [2] | 65 |
| 4-(1,1-DIMETHYLETHYL)-1-CYCLOHEXYLE ACETATE | 25 |
| 4-(2,6,6-TRIMETHYL-1-CYCLOHEXEN-1-YL)-2-BUTANONE | 20 |
| AMBRINOL | 15 |
| AMBRINOL OXYDE | 10 |
| POLYSANTOL ® [3] | 10 |
| CASHMERAN ® [4] | 9 |
| EXALTOLIDE ® [5] | 9 |
| HABANOLIDE ® [6] | 8 |

TABLE 1-b-continued

Composition of fragrance F2

| Ingredients | Parts |
|---|---|
| (+−)-4-(2,6,6-TRIMETHYL-2-CYCLOHEXEN-1-YL)-2-BUTANONE | 4 |
| (+)-(1S, 6R)-3,7,7-TRIM ETHYL-BICYCLO[4.1.0]HEPT-3-ENE | 4 |
| ISOBUTYLQUINOLEINE | 3 |
| LINALYL ACETATE | 3 |
| (Z)-3,7,11-TRIMETHYL-1,6,10-DODECATRIEN-3-OL | 2 |
| BENZYLACETONE | 2 |
| 3,6,8,8-TETRAMETHYLOCTAHYDRO-1H-3A,7-METHANOAZULEN-6-OL | 2 |
| 2,3,3-TRIMETHYL-1-INDANONE | 2 |
| BACDANOL [7] | 1 |
| ALPHA TERPINYL ACETATE | 1 |
| TOTAL PARTS | 10075 |

[1] 1-(octahydro-2,3,8,8-tetramethyl-2-naphtalenyl)-1-ethanone, International Flavors & Fragrances, USA
[2] (—)-(8R)-8,12-epoxy-13,14,15,16-tetranorlabdane, Firmenich SA, Geneva, Switzerland
[3] 3,3-dimethyl-5-(2,2,3-trimethyl-3-cyclopenten-l-yl)-4-penten-2-ol, Firmenich SA, Geneva, Switzerland
[4] 1,2,3,5,6,7-hexahydro-1,1,2,3,3-pentamethyl-4-indenone, International Flavors & Fragrances, USA
[5] Pentadecanolide, Firmenich SA, Geneva, Switzerland
[6] Pentadecanolide, Firmenich SA, Geneva, Switzerland
[7] 2-éthyl-4-(2,2,3-triméthyl-3-cyclopentèn-l-yl)-2-butèn-1-ol, International Flavors & Fragrances, USA TABLE 1-c Composition of fragrance F3

| Ingredients | Parts |
|---|---|
| 1,4-DIOXACYCLOHEPTADECANE-5,17-DIONE | 1000 |
| CEDAR oil | 30 |
| BACDANOL [1] | 280 |
| BENZYL ACETATE | 260 |
| BENZYL ALCOHOL | 30 |
| BENZYL SALICYLATE | 330 |
| BENZYLDIMETHYLCARBINOL ACETATE | 90 |
| CARYOPHYLLENE | 20 |
| CITRONELLOL | 350 |
| CITRON ELLYL ACETATE | 20 |
| CITRONELLYL FORMATE | 6 |
| COUMARIN | 4 |
| CUBEBOL | 2 |
| CYCLOSAL | 10 |
| DIHYDROLINALOOL | 1 |
| DIHYDROMYRCENOL | 100 |
| DIPROPYLENGLYCOL | 2430 |
| 4-(1,1-DIMÉTHYLÉTHYL)-1-CYCLOHEXYLE ACETATE | 380 |
| ETHYLSAFRANATE | 50 |
| EUGENOL | 30 |
| FLOROL ® [2] | 10 |
| GERANIAL | 1 |
| GERANIOL | 70 |
| GERANYL ACETATE | 40 |
| HABANOLIDE ® [3] | 310 |
| HELVETOLIDE ® [4] | 1 |
| HEXYLCINNAMIC ALDEHYDE | 1020 |
| INDOLE | 5 |
| ISO E SUPER [5] | 760 |
| ISOBUTYLQUINOLEINE | 2 |
| ISOPROPYL MYRISTATE | 40 |
| LILIAL | 30 |
| LINALOOL | 110 |
| LINALYL ACETATE | 110 |
| LYRAL | 30 |
| METHYL PH ENYLACETATE | 2 |

TABLE 1-c-continued

Composition of fragrance F3

| Ingredients | Parts |
| --- | --- |
| METHYLIONONE ALPHA ISO | 180 |
| METHYLISOEUGENOL | 10 |
| METHYL 2,4-DIHYDROXY-3,6-DIMETHYLBENZOATE | 10 |
| 1-[(1RS,6SR)-2,2,6-TRIMETHYLCYCLOHEXYL]-3-HEXANOL | 30 |
| CYCLOHEXYLIDENE(PHENYL)ACETONITRILE | 20 |
| PHENYLETHYL ACETATE | 10 |
| PHENYLETHYL ALCOHOL | 620 |
| PHENYLETHYL PHENYLACETATE | 40 |
| POLYSANTOL ® | 130 |
| RHODINOL G | 9 |
| 4-METHYL-2-(2-METHYL-1-PROPEN-1-YL)TETRAHYDRO-2H-PYRAN | 10 |
| 2,3,3-TRIMETHYL-1-INDANONE | 9 |
| (+−)-3-MÉTHYL-5-(2,2,3-TRIMÉTHYL-3-CYCLOPENTEN-1-YL)-2-PENTANOL [6] | 10 |
| SANDELA ® [7] | 140 |
| STYRALLYL ACETATE | 40 |
| (2,2-DIMÉTHOXYÉTHYL)BENZÈNE | 8 |
| VERTOFIX | 2 |

[1] 2-ethyl-4-(2,2,3-triméthyl-3-cyclopentn-1-yl)-2-buten-1-ol, International Flavors & Fragrances, USA
[2] (+−)-tetrahydro-2-isobutyl-4-methyl-4(2H)-pyranol, Firmenich SA, Geneva, Switzerland
[3] Pentadecanolide, Firmenich SA, Geneva, Switzerland
[4] (1S,1'R)-2-[1-(3',3'-dimethyl-1'-cyclohexyl)ethoxy]-2-methylpropyl propanoate, Firmenich SA, Geneva, Switzerland
[5] 1-(octahydro-2,3,8,8-tetramethyl-2-naphtalenyl)-1-ethanone, International Flavors & Fragrances, USA
[6] Givaudan SA
[7] 5-(2,2,3-Trimethyl-3-cyclopentenyl)-3-methylpentan-2-ol, GIVAUDAN SA

TABLE 1-d

Composition of fragrance F4

| Ingredient | Parts |
| --- | --- |
| 10-UNDECENAL | 2 |
| AM BROX ® [1] | 260 |
| ASTROTONE | 2570 |
| BENZYL ACETATE | 20 |
| BENZYL ALCOHOL | 6 |
| BENZYL SALICYLATE | 110 |
| CITRONELLOL | 1 |
| CITRON ELLYL ACETATE | 8 |
| COUMARIN | 7 |
| DIPROPYLENGLYCOL | 5670 |
| 4-(1,1-DIMÉTHYLÉTHYL)-1-CYCLOHEXYLE ACETATE | 260 |
| ETHYLVANILLINE | 4 |
| GERANIOL | 6 |
| GERANYL ACETATE | 1 |
| HELIOTROPIN | 2 |
| HEXYLCINNAMIC ALDEHYDE | 40 |
| HYDROXYCITRONELLAL | 6 |
| ISOEUGENYL ACETATE | 2 |
| LILIAL | 20 |
| LINALYL ACETATE | 10 |
| LYRAL | 1 |
| METHYLIONONE ALPHA ISO | 30 |
| PHENOXYETHYL ISOBUTYRATE | 3 |
| PHENYLETHYL ACETATE | 2 |
| PHENYLETHYL ALCOHOL | 40 |
| ROSINOL [2] | 100 |
| SAN DELA ® | 9 |
| STYRALLYL ACETATE | 8 |
| TONALIDE [3] | 560 |
| UNDECALACTONE GAMMA | 2 |
| (2,2-DIMETHOXYETHYL)BENZENE | 1 |
| Total parts | 9758 |

[1] (—)-(8R)-8,12-epoxy-13,14,15,16-tetranorlabdane, Firmenich SA, Geneva, Switzerland
[2] (+−)-2,2,2-trichloro-1-phenylethyl acetate
[3] 1-(3,5,5,6,8,8-hexamethyl-5,6,7,8-tetrahydro-2-naphthalenyl)ethanone

Example 1

Preparation of Perfuming Compositions and Evaluation of the Stability Performance

TABLE 2

Compositions comprising perfume, TCD alcohol DM, Hexylene glycol vs comparative composition comprising perfume, TCD alcohol DM, and dipropylene glycol (DiPG)

| | | Comparative composition X (% wt) | Composition A (% wt) | Composition B (% wt) |
| --- | --- | --- | --- | --- |
| Viscosifying agent | Tricyclodecanedimethanol alcohol [1] | 60 | 60 | 60 |
| Perfumery carrier | Dipropylene glycol (DiPG) [2] | 20 | | |
| | Hexylene glycol [3] | | 20 | 19.2 |
| Aqueous phase | Water | | | 0.8 |
| Perfume oil | Fragrance F1 [4] | 20 | 20 | 20 |
| | Heating temperature for TCD Alcohol DM | 70° C. | 70° C. | 70° C. |

[1] TCD alcohol DM, Origin: Oxea
[2] Origin: Firmenich SA, Geneva, Switzerland
[3] Origin: Firmenich SA, Geneva, Switzerland
[4] See table 1-a All the compositions listed in table 2 were visually assessed transparent clear before letting the samples at room temperature and observe their evolution.

It appeared that the comparative composition X containing DiPG starts to precipitate (slight cloudy aspect) after about 14 days at room temperature. Strong precipitation was observed after 46 days.

By contrast, composition A (where DiPG was replaced by hexylene glycol) starts to precipitate (slight cloud aspect) only after 35 days; i.e long after the precipitation of comparative composition X. Strong precipitation occurred after 58 days.

In composition B, part of hexylene glycol was replaced by water. The sample stays clear for 85 days (i.e. about 3 months).

The above results underlines that the presence of hexylene glycol in the perfuming compositions prevents significantly the recrystallization of TCD alcohol DM in said composition upon storage.

TABLE 3

Compositions comprising perfume, TCD alcohol DM, hexylene glycol vs comparative composition comprising perfume, TCD alcohol DM, dipropylene glycol and glycerol

|  |  | Comparative composition Y (% wt) | Composition C (% wt) |
|---|---|---|---|
| Viscosifying agent | Tricyclodecanedimethanol alcohol [1] | 55 | 58 |
| Perfumery carrier | DiPG [2] | 20 |  |
|  | Hexylene glycol [3] |  | 21 |
|  | Glycerol [4] | 5 |  |

TABLE 3-continued

Compositions comprising perfume, TCD alcohol DM, hexylene glycol vs comparative composition comprising perfume, TCD alcohol DM, dipropylene glycol and glycerol

|  |  | Comparative composition Y (% wt) | Composition C (% wt) |
|---|---|---|---|
| Aqueous phase | Water |  |  |
| Perfume oil | Fragrance F1 [5] | 20 | 21 |
|  | Heating temperature for TCD Alcohol DM | 70° C. | 70° C. |

[1] TCD alcohol DM, Origin: Oxea
[2] Origin: Firmenich SA, Geneva, Switzerland
[3] Origin: Firmenich SA, Geneva, Switzerland
[4] Origin: Acros Organics
[5] See table 1-a In comparative composition Y, TCD alcohol DM was partially replaced by Glycerol, using also DiPG as co-solvent. The crystallization occurs in that case after about 30 days at room temperature. As a comparison, a composition according to the invention containing hexylene glycol instead of DiPG shows a very slight precipitation after about 52 days at room temperature.

Example 2

Preparation of Perfuming Compositions According to the Invention Using Different Fragrances Perfuming compositions were prepared using different fragrances.

TABLE 4

Compositions comprising TCD alcohol DM, hexylene glycol, water and fragrance

|  |  | Composition D (% wt) | Composition E (% wt) | Composition F (% wt) |
|---|---|---|---|---|
| Viscosifying agent | tricyclodecanedimethanol alcohol [1] | 60 | 60 | 60 |
| Perfumery carrier | Hexylene glycol [2] | 19.2 | 19.2 | 19.2 |
| Aqueous phase | Water | 0.8 | 0.8 | 0.8 |
| Perfume oil | Fragrance F2 [3] | 20 |  |  |
|  | Fragrance F3 [4] |  | 20 |  |
|  | Fragrance F4 [5] |  |  | 20 |
|  | Heating temperature for TCD Alchol DM | 70° C. | 70° C. | 70° C. |

[1] TCD alcohol DM, Origin: Oxea
[2] Origin: Firmenich SA, Geneva, Switzerland
[3] See table 1-b
[4] See table 1-c
[5] See table 1-d Composition D-F according to the invention were stable for at least 28 days at room temperature. These results underline that perfuming compositions according to the invention can be prepared with fragrances covering a broad log P range.

Example 3

Preparation of Perfuming Compositions and Evaluation of the Stability Performance

TABLE 5

Compositions comprising TCD alcohol DM, hexylene glycol, (water) and fragrance vs Composition comprising TCD alcohol DM, dipropylene glycol, water and fragrance

| | | Comparative composition Z (% wt) | Composition G (% wt) | Composition H (% wt) |
|---|---|---|---|---|
| Viscosifying agent | Tricyclodecanedimethanol alcohol [1] | 60 | 60 | 60 |
| Perfumery carrier | DiPG [2] | 20 | 0 | 0 |
| | Hexylene glycol [3] | 0 | 20 | 19.2 |
| Perfume oil | Fragrance F3 [4] | 20 | 20 | 20 |
| Aqueous phase | Water | 0 | 0 | 0.8 |
| | Heating temperature for TCD Alcohol DM | 90° C. | 90° C. | 90° C. |

[1] TCD alcohol DM, Origin: Oxea
[2] Origin: Firmenich SA, Geneva, Switzerland
[3] Origin: Firmenich SA, Geneva, Switzerland
[4] See table 1-c Crystallization occurs after 5 months of storage at room temperature for comparative composition Z whereas compositions G and H present no recrystallization even after 8 months storage at room temperature.

The invention claimed is:

1. A perfuming composition comprising:
   a viscosifying agent comprising tricyclodecanedimethanol alcohol,
   a perfume oil comprising at least one perfuming ingredient,
   at least one perfumery carrier comprising hexylene glycol, and
   optionally, a perfuming adjuvant,
   wherein the weight ratio between tricyclodecanedimethanol alcohol and hexylene glycol in the perfuming composition is from 0.1 to 15.

2. The perfuming composition according to claim 1 comprising at least 5% by weight of tricyclodecanedimethanol alcohol based on the total weight of the perfuming composition.

3. The perfuming composition according to claim 1 comprising up to 50% by weight of the perfume oil based on the total weight of the perfuming composition.

4. The perfuming composition according to claim 1 comprising up to 40% by weight of hexylene glycol based on the total weight of the perfuming composition.

5. The perfuming composition according to claim 1, wherein the perfumery carrier further comprises at least one co-solvent selected from the group consisting of dipropylene glycol, glycerol, 1,2-pentanediol, 1,2-hexanediol, D,L-1,2-isopropylidene glycerol, propanediol, butanediol and mixtures thereof.

6. The perfuming composition according to claim 5, wherein the co-solvent is dipropylene glycol.

7. The perfuming composition according to claim 5, wherein the co-solvent is used in an amount between 5 and 30% by weight based on the total weight of the composition.

8. The perfuming composition according to claim 1 further comprising an aqueous phase.

9. The perfuming composition according to claim 8, wherein the aqueous phase is used in amount between 0.01% and 1% by weight based on the total weight of the composition.

10. The perfuming composition according to claim 1, wherein the perfuming composition has a viscosity comprised between 500 and 5000 mPa·s at 20° C.

11. The perfuming composition according to claim 1, wherein the perfumery adjuvant is selected from the group consisting of colors, preservatives, pH adjusters, antioxidants, chelating agents, UV filters, quenchers, silicon oils, and mixture thereof.

12. A consumer product comprising the perfuming composition as defined in claim 1.

13. The consumer product of claim 12, wherein the consumer product is in the form of a fine fragrance product or an air freshener.

14. A process for manufacturing a perfuming composition comprising the steps of:
   (i) Heating tricyclodecanedimethanol alcohol and
   (ii) Cooling down the tricyclodecanedimethanol obtained in step i) before adding a perfume oil,
   wherein hexylene glycol is added in step (i) or in step (ii), and
   wherein the weight ratio between tricyclodecanedimethanol alcohol and hexylene glycol in the perfuming composition is from 0.1 to 15.

15. The process according to claim 14, wherein the tricyclodecanedimethanol alcohol is heated at a temperature between 90° C. and 120° C.

16. The process according to claim 15, wherein the tricyclodecanedimethanol alcohol is heated at a temperature between 100° C. and 120° C.

17. The process according to claim 14, wherein the tricyclodecanedimethanol alcohol is heated at a temperature between 70° C. and 120° C.

18. A consumer product obtained by the process defined in claim 14.

19. The consumer product of claim 18, wherein the consumer product is in the form of a fine fragrance product or an air freshener.

20. A method of using hexylene glycol in a perfuming composition comprising tricyclodecanedimethanol alcohol and a perfume oil, the method comprising using the hexylene glycol to prevent crystallization of the perfuming composition.

\* \* \* \* \*